US00PP17703P3

(12) United States Plant Patent
Larsen

(10) Patent No.: US PP17,703 P3
(45) Date of Patent: May 8, 2007

(54) ***OSTEOSPERMUM* PLANT NAMED 'SUNNY GOLDEN SERENA'**

(50) Latin Name: *Osterospermum ecklonis*
Varietal Denomination: Sunny Golden Serena

(75) Inventor: Bjarne Nyholm Larsen, Odense N (DK)

(73) Assignee: Sunny Gronnegyden APS, Odense N (DK)

( * ) Notice: Subject to any disclaimer, the term of this patent is extended or adjusted under 35 U.S.C. 154(b) by 66 days.

(21) Appl. No.: 11/094,122

(22) Filed: Mar. 31, 2005

(65) Prior Publication Data

US 2006/0225177 P1 Oct. 5, 2006

(51) Int. Cl.
*A01H 5/00* (2006.01)

(52) U.S. Cl. ..... Plt./360
(58) Field of Classification Search ..... Plt./360
See application file for complete search history.

(56) References Cited

PUBLICATIONS

Extract from the Register of the Community Variety Rights dated Jan. 31, 2005 (1 pg.), together with the Certificate on the Grant of Community Plant Variety Rights for 'Sunny Golden Serena' (1 pg.).

*Primary Examiner*—Kent Bell
(74) *Attorney, Agent, or Firm*—Foley & Lardner LLP

(57) ABSTRACT

A new distinct cultivar of *Osteospermum* plant named 'Sunny Golden Serena', characterized by its unique gray-orange color combination of upper and underside of ray florets: (when opening) upperside RHS 163D with stripes of RHS 164B and underside RHS N163 with stripes of RHS 165A; (fully opened) upperside RHS 164D with stripes of RHS 164A and underside center stripe RHS 165B with margins RHS 164C; upright, compact and globular plant habit; dense and bushy growth habit, mainly due to upright stems; moderately vigorous growth habit, but less need for chemical growth retardation; and high number of inflorescences per plant.

5 Drawing Sheets

Figure 1:
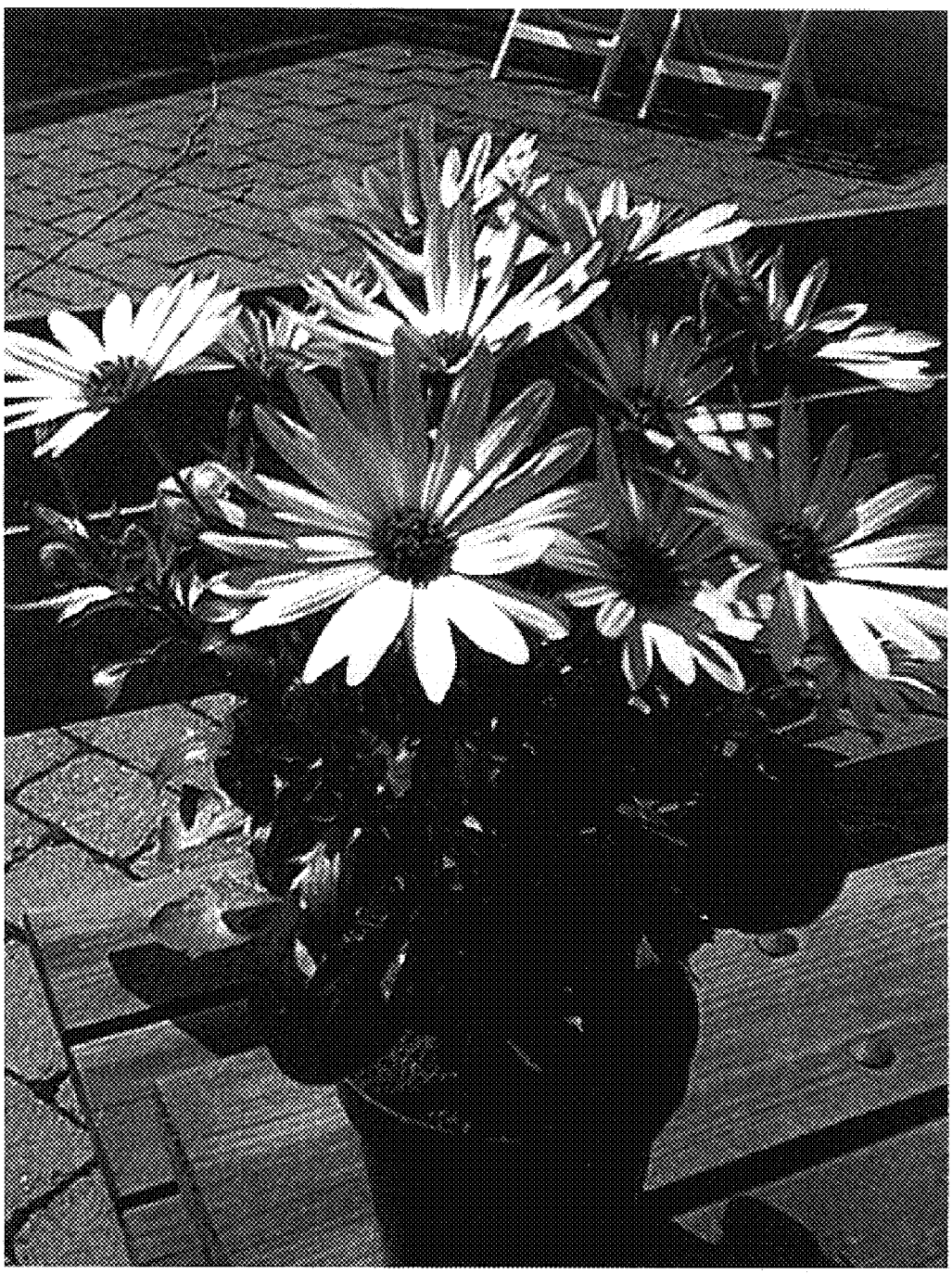

Botanical designation: *Osteospermum ecklonis.*
Variety denomination: 'Sunny Golden Serena'.

BACKGROUND OF THE INVENTION

The present Invention relates to a new and distinct cultivar of *Osteospermum* plant, botanically known as *Osteospermum ecklonis* (*DC*) *T. Norl.,* commonly known as Cape Daisy and hereinafter referred to by the variety denomination 'Sunny Golden Serena'.

The new *Osteospermum* cultivar is a product of a planned breeding program conducted by the Inventor, Bjarne Nyholm Larsen, in Stige, Denmark. The objective of the breeding program is to create new compact *Osteospermums* with continuous flowering, good postproduction longevity and attractive inflorescence coloration.

The new *Osteospermum* cultivar originated as a naturally occurring whole plant mutation found as a single *Osteospermum* plant in a production batch of *Osteospermum ecklonis* (*DC*) *T. Norl.* designated 'Sunny Serena' (patented, and disclosed in U.S. Plant Pat. No. 15,693 and CPVO Registration Number 10371) in March of 2002 in Stige, Denmark. The Inventor selected the new *Osteospermum* cultivar in June of 2002 on the basis of its attractive inflorescence color, good postproduction longevity, continuous flowering and upright, compact, freely branching growth habit.

Asexual reproduction of the new *Osteospermum* cultivar by terminal cuttings taken and propagated at trial production batches in Stige, Denmark, since 2003 has demonstrated that the combination of characteristics as herein disclosed for the new cultivar are firmly fixed and retained through successive generations of asexual reproduction. The new *Osteospermum* cultivar reproduces true-to-type.

SUMMARY OF THE INVENTION

The following traits have been repeatedly observed and are determined to be the unique characteristics of 'Sunny Golden Serena'. These characteristics in combination distinguish 'Sunny Golden Serena' as a new and distinct cultivar:

1. Unique gray-orange color combination of upper and underside of ray florets: (when opening) upperside RHS 163D with stripes of RHS 164B and underside RHS N163 with stripes of RHS 165A; (fully opened) upperside RHS 164D with stripes of RHS 164A and underside center stripe RHS 165B with margins RHS 164C.
2. Upright, compact and globular plant habit;
3. Dense and bushy growth habit, mainly due to upright stems;
4. Moderately vigorous growth habit; but less need for chemical growth retardation; and
5. High number of inflorescences per plant.

Plants of the *Osteospermum* cultivar 'Sunny Golden Serena' differ from plants of the cultivar 'Sunny Serena' by the traits characterised in Table 1 below:

TABLE 1

| Trait | 'Sunny Golden Serena' | 'Sunny Serena' (patented) |
|---|---|---|
| Number of Lateral Branches | 7 primary, 12 secondary | 4 primary, 7 secondary |
| Leaf Length | 3 to 8 cm | 2 to 4 cm |
| Inflorescence Width | 7 to 8 cm | 6 to 7 cm |
| Quantity of Inflorescences and Buds per Plant | 35 | 20 |
| Bud Color | From RHS 144A to RHS N144B, yellow-green | From RHS 145C to RHS 154B, yellow-green |
| Ray Floret Color: | Shades of gray-orange | Shades of gray-yellow, yellow-white and gray-orange |
| Disc floret Color: | Gray-orange tips with gray-white bases | Silvery gray and gray-white |
| Anther Color: | RHS 200B, brown | RHS N99B, blue |
| Stigma Color: | RHS 200B, brown | RHS N187A, purple |

Of the many commercial cultivars known to the Inventor, the most similar in comparison to the *Osteospermum* cultivar 'Sunny Golden Serena' is the *Osteospermum ecklonis* (*DC*) *T. Norl.* cultivar 'Sunny Nathalie' (patented, and disclosed in U.S. Plant Pat. No. 13,358 and CPVO Registration Number 2003/10480). In side-by-side comparisons conducted by the Inventor in Stige Denmark, plants of the cultivar 'Sunny Golden Serena' and the cultivar 'Sunny Nathalie' differ primarily in inflorescence color. Plants of the 'Sunny Golden Serena' have a striking color combinations of golden gray-orange ray florets and disc florets with orange pollen whereas plants of 'Sunny Nathalie' have gray-purple ray florets with violet-blue disc florets with yellow-orange pollen.

BRIEF DESCRIPTION OF THE PHOTOGRAPHS

The accompanying colored photographs illustrate the overall appearance of the new *Osteospermum* cultivar 'Sunny Golden Serena' showing the colors as true as is reasonably possible with colored reproductions of this type. Colors in the photographs may differ slightly from the color values cited in the detailed botanical description which accurately describe the color of the new *Osteospermum* cultivar 'Sunny Golden Serena'.

The first photograph (FIG. 1) shows a side perspective view of a typical flowering plant of 'Sunny Golden Serena' as grown in an 11 cm pot.

Figure 2:
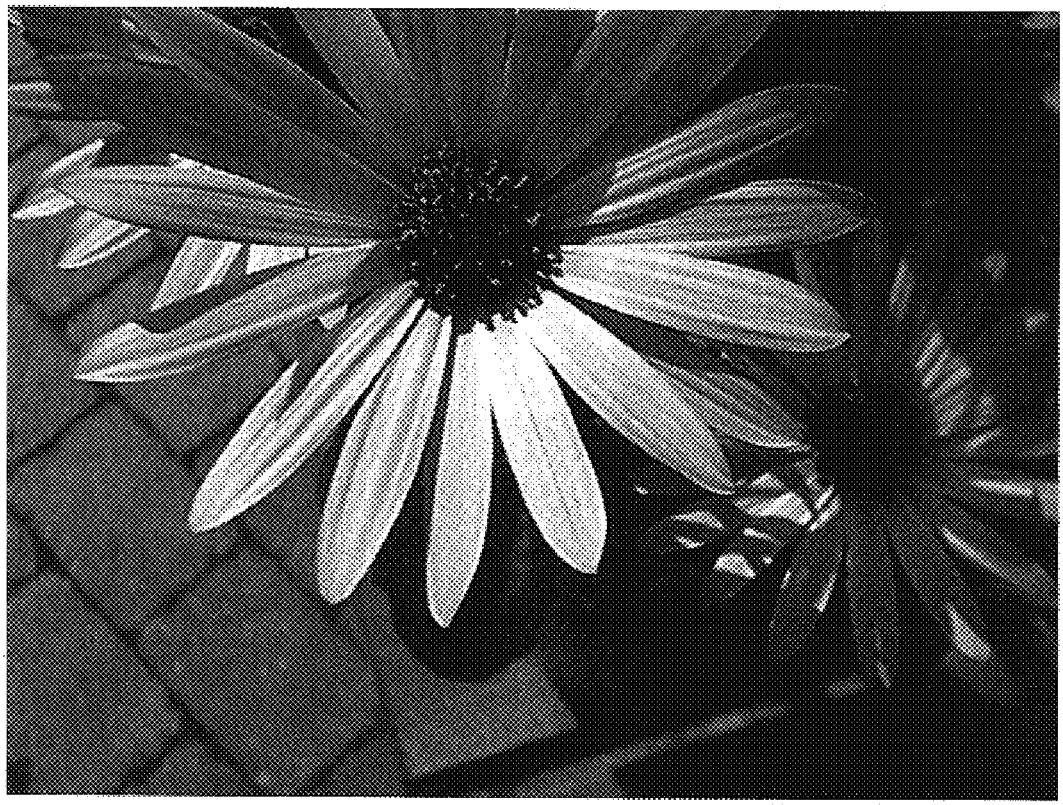

The second photograph (FIG. 2) shows a close-up view of the upperside of the ray florets of 'Sunny Golden Serena'.

Figure 3:
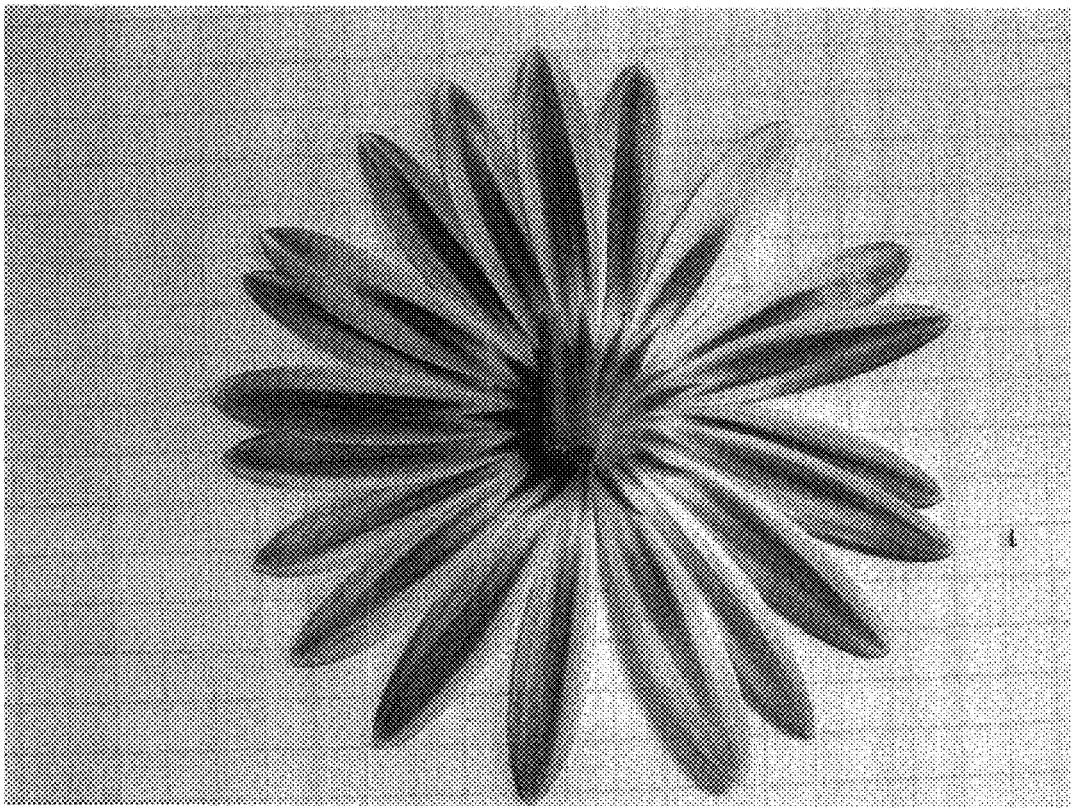

The third photograph (FIG. 3) shows a close-up view of the underside of the ray florets of 'Sunny Golden Serena'.

Figure 4:
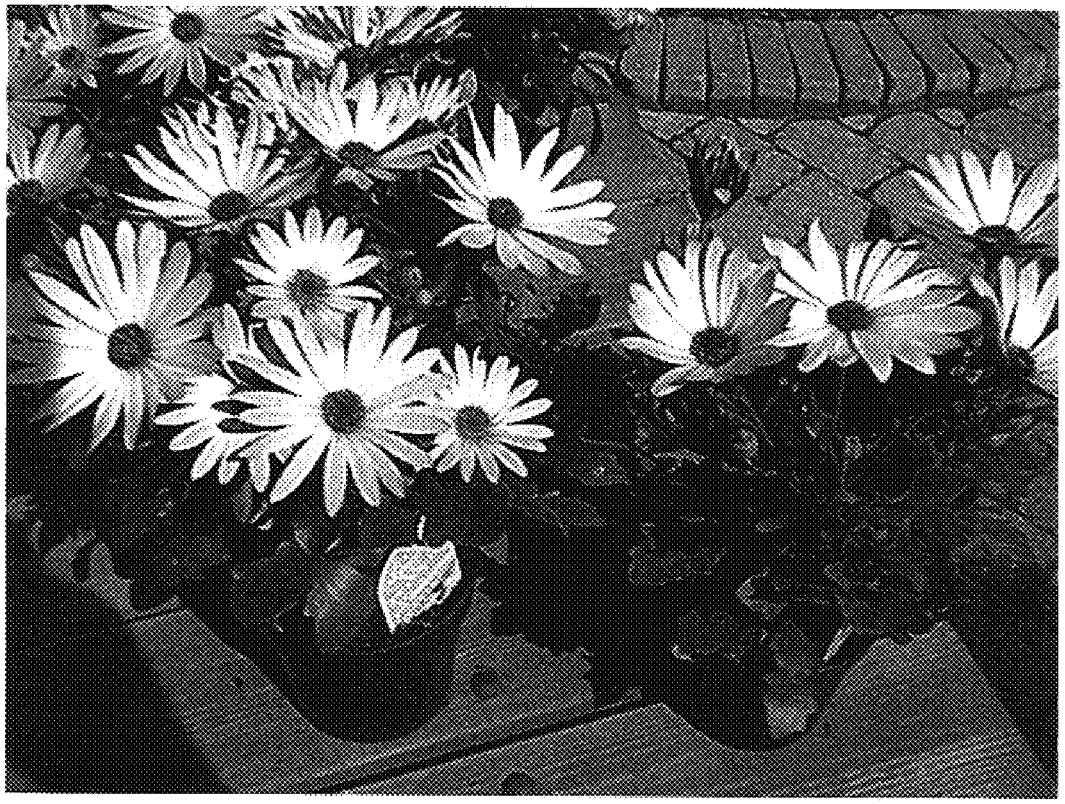

The fourth photograph (FIG. 4) shows a side perspective view of a typical flowering plant of 'Sunny Golden Serena' (on the left) compared to a typical flowering plant of 'Sunny Serena' (on the right).

Figure 5:
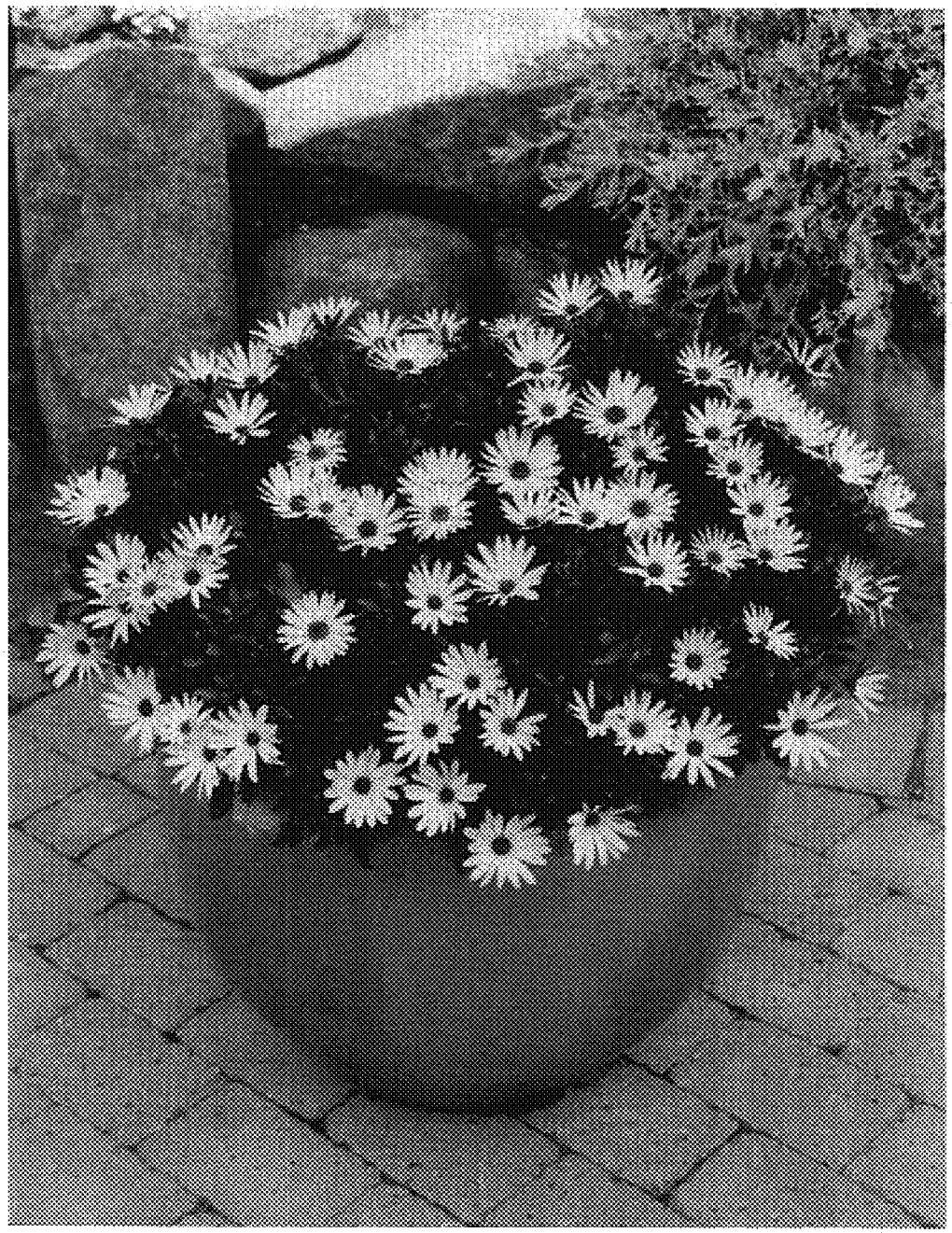

The fifth photograph (FIG. 5) shows a side perspective view of numerous potted plants of 'Sunny Golden Serena' as grown in a large display pot.

DETAILED BOTANICAL DESCRIPTION

Plants of the new *Osteospermum* cultivar 'Sunny Golden Serena' have not been observed under all possible environmental conditions. The phenotype may vary somewhat with variations in environment such as temperature, light intensity, daylength, and fertility level without any variance in the genotype of the plant.

The aforementioned photographs, together with the following observations, measurements and values describe plants of the new *Osteospermum* cultivar 'Sunny Golden Serena' as grown in a heated and lighted, glass-covered greenhouse in Fyn, Denmark, under conditions which closely approximate those generally used in commercial practice. Plants of the new *Osteospermum* cultivar 'Sunny Golden Serena' were grown in natural long days with 15 to 20 hours of daylight. Chlormequat treatments 3×0.5% drench were also used when growing 'Sunny Golden Serena'.

The age of the 'Sunny Golden Serena' plants described is 20 weeks old after cutting and grown in 11 cm pots. The photographs and descriptions were taken during the spring season when outdoor day temperatures range from 18 to 22° C. and when outdoor night average temperature range from 16 to 18° C.

Color references are made to The Royal Horticultural Society Colour Chart (R.H.S.), 4$^{th}$ ed., except where general colors of ordinary significance are used.

Botanical classification: *Osteospermum ecklonis.*

Parentage: *Osteospermum ecklonis* (*DC*) *T. Norl.* designated 'Sunny Serena' (patented, and disclosed in U.S. Plant Pat. No. 15,693 and CPVO Registration Number 10371).

Propagation:

*Type of cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Non-hardy perennial, potted or garden bedding plant. Globular, upright, with basal branching plant habit. *Osteospermum* inflorescences in composite heads. Freely branching with lateral flowering branches forming at every node; dense and bushy.

*Crop time.*—After rooting, about 20 weeks are required to produce finished flowering plants in 11 cm pots.

*Plant height* (*soil level to top of plant plane*).—About 17 cm.

*Plant spread* (*width*).—About 17 cm.

*Lateral branches.*—Quantity per plant: 7 primary and 12 secondary (flowering). Length (primary): 3 cm. Length (secondary): 7 to 12 cm. Diameter (primary and secondary): 4 to 5 mm. Quantity of leaves: 10 to 15 per lateral branch.

*Internode.*—Length: 3 mm.

*Stem.*—Shape: Round. Strength: Strong. Aspect: (main stem) upright, branches at 70–80° angle. Texture: Smooth, glabrous. Color: RHS 144C, yellow-green.

*Vigor.*—Moderately vigorous growth rate.

*Foliage description.*—Alternate (⅕ whorl), single, pinnate venation. Length: 3 to 8 cm. Width: 1.2 cm. Shape: Obovate to spatulate, 4 to 6 acuminate teeth. Apex: Obtuse. Base: Attenuate, decurrent. Margin: Broadly dentate (2 to 3 lobes on each side). Texture (both sides and edges): Pubescent with scattered short, stiff hairs. Color: Young foliage, upperside RHS 147A, yellow-green; underside RHS 148D, yellow-green. Mature foliage, upperside RHS 139A, green; underside RHS 147A, yellow-green.

*Venation.*—Color: upperside RHS 147C, yellow-green; underside RHS 148B, yellow-green. Pattern: Pinnate.

*Petiole.*—Length: 10 to 20 mm. Diameter: 2 to 4 mm. Shape: flat, winged. Texture: Scattered short stiff hairs. Color: RHS 145B, yellow-green.

Inflorescence description:

*Inflorescence number per plant.*—About 35.

*Inflorescence arrangement and shape.*—Tubular disc florets and flat, lanceolate ray florets in composite daisy heads in leaf axils; with 15 parted involucre. Inflorescences face upright to 80° angle from vertical.

*Natural flowering season.*—Continuous throughout the spring and summer. Season can be extended by vernalization and long day treatments.

*Rate of inflorescence opening.*—About 3 per week.

*Inflorescence longevity on the plant.*—5 to 10 days; however, longevity of individual inflorescence is highly dependent on temperature and light conditions. Inflorescence persistent.

*Fragrance.*—Weak, fresh lemon fragrance.

*Number of inflorescence heads per lateral stem.*—2.

*Inflorescence size.*—Height. 6 mm capitulum. Diameter: 7 to 8 cm capitulum; 1 mm single disc floret.

Buds:

*Quantity per lateral stem.*—5. Length: up to 12 mm. Diameter: up to 10 mm. Rate of opening: 2 per plant per week. Shape: Globular. Color: From RHS 144A (base) to RHS N144B, yellow green, charging to RHS N199D, gray-brown, before anthesis.

Inflorescences:

Ray florets:

*Typical number of ray florets per inflorescence.*—About 20. Observed number of ray florets per inflorescence: 18 to 22. Arrangement: Sympetalous. Appearance: 3 or more furrows. Texture: Smooth, matte. Length: About 25 to 28 mm. Width (diameter): About 8 mm. Shape: Elliptic. Apex: Rounded with slight emargination. Base: Fused. Margin: Entire. Ray floret color: Shades of golden gray-orange; (when opening) upperside RHS 163D with stripes of RHS 164B and underside RHS N163 with stripes of RHS 165A; (fully opened) upperside RHS 164D with stripes of RHS 164A and underside center stripe RHS 165B with margins RHS 164C. Fading to RHS N199C, gray-brown.

Disc florets:

*Typical number of discs florets per inflorescence.*—55. Observed number of discs florets per inflorescence: 40 to 62. Arrangement: Sympetalous. Appearance: Translucent. Texture: Smooth, matte. Length: About 12 mm. Width (diameter): About 3 mm. Shape: Free tips attenuate. Base: Fused. Margin: free tips entire. Disc floret color: (when opening and fully opened) upperside and underside RHS 165A, gray-orange tips, with bases RHS 156A, gray-white.

*Phyllary.*—Appearance: Involucre, 15 lanceolate units. Quantity of phyllaries: 15. Length: 6 to 12 mm. Width: 1 to 3 mm. Overall shape: Lanceolate. Apex: Acuminate. Base: Fused. Margin: Entire. Color: RHS 137D, green (no difference in RHS color designation depending on immature v. mature and upperside v. underside).

*Peduncle.*—Length: About 5 to 7 cm. Diameter: About 2 mm. Strength: Strong, stiff. Angle: 0 to 80° from vertical. Color: RHS 144C, yellow-green.

Reproductive organs:

*Androecium.*—Location: Disc florets only. Stamen: Quantity: 5, fused. Anthers: Shape: Linear, fused. Length: About 2 mm. Color: RHS 200B, brown. Pollen: Amount: Good production, plenty. Color: RHS 25A, orange.

*Gynoecium.*—Location: Ray and disc florets. Pistil: Quantity: 1. Length: About 4 mm. Stigma: Shape: Brush-like, cleft. Color: RHS 200B, brown. Style: Length: 2 mm. Color: Inconspicuous. Ovary: Color: RHS 2D, green-yellow.

*Seeds.*—Quantity: many, 10 to 20 per inflorescence. Length: 2 to 3 mm. Diameter: About 1 mm. Texture: Smooth and glabrous. Color: Brown-gray.

*Fruit.*—None.

*Growth retardants.*—Chlormequat 3×0.5% drench.

Weather tolerance: Plants of the new *Osteospermum* have exhibited good tolerances to drought, rain and wind, with low temperature resistance to 1° C.

Disease/pest resistance: Good.

Disease/pest susceptibility: Low.

I claim:

1. A new and distinct cultivar of *Osteospermum* plant named 'Sunny Golden Serena', as illustrated and described herein.

* * * * *